(12) United States Patent
Graumann et al.

(10) Patent No.: US 7,048,440 B2
(45) Date of Patent: May 23, 2006

(54) C-ARM X-RAY DEVICE

(75) Inventors: Rainer Graumann, Hochstadt (DE); Udo Heinze, Baiersdorf (DE); Peter Nögel, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 45 days.

(21) Appl. No.: 10/798,546

(22) Filed: Mar. 11, 2004

(65) Prior Publication Data

US 2004/0202284 A1  Oct. 14, 2004

Related U.S. Application Data

(60) Provisional application No. 60/454,053, filed on Mar. 12, 2003.

(51) Int. Cl.
*H05G 1/02* (2006.01)
(52) U.S. Cl. .................... 378/197; 378/193; 378/196
(58) Field of Classification Search ............ 378/196, 378/197, 206, 198, 4, 193, 205
See application file for complete search history.

(56) References Cited

U.S. PATENT DOCUMENTS 6,139,183 A * 10/2000 Graumann .................. 378/206
6,382,835 B1   5/2002 Graumann et al.

FOREIGN PATENT DOCUMENTS

DE         10003524 A1 *  8/2001

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

The invention concerns a C-arm x-ray device with a non-isocentric C-arm on which an x-ray source is positioned and that can be orbitally or angularly rotated, whereby the C-arm x-ray device comprises a device fashioned to horizontally adjust the C-arm (which enables an adjustment of the C-arm within the plane of the C-arm) and a device fashioned to vertically adjust the C-arm, where the horizontal adjustment device and the vertical adjustment device are fashioned such that they can automatically move the central x-ray beam of the x-ray source back into the isocenter, given an orbital or angulatory rotation of the C-arm via the horizontal and vertical adjustment device. An appertaining method is also provided.

9 Claims, 2 Drawing Sheets

C-ARM X-RAY DEVICE

CROSS REFERENCE TO RELATED APPLICATIONS

The present application claims the benefit of U.S. Provisional Application No. 60/454,053, filed Mar. 12, 2003.

BACKGROUND OF THE INVENTION

The invention concerns a C-arm x-ray device for 3D imaging.

X-ray detectors are used to generate images of a transirradiated subject or body. The x-rays pass through the subject or patient and then strike an image detector on which they form a two-dimensional projection of the transirradiated volume.

Three-dimensional image data can be generated using a plurality of two-dimensional projections of the same x-ray volume. The individual two-dimensional image data are evaluated using a computer to generate a three-dimensional image. For this, the two-dimensional image data must exist digitized, which is why digital image sensors are used and not analog film/foil systems. Digital image sensors directly generate digital, pixelated image data as soon as x-ray radiation is incident upon them. These can be directly fed to a computer for further evaluation.

The generation of three-dimensional image data from two-dimensional x-ray projections assumes that the volume to be reconstructed has in fact been transirradiated in each projection. Stated more precisely, in each individual projection, the central axis of the x-ray beam must pass through a point that it also passes through in all other projections. In order to generate the individual two-dimensional projections, the central x-ray beam thus assumes different orientations in space, whereby a common point of intersection of the central x-ray beam is given for all different orientations. This point of intersection is designated as an isocenter. The specified procedure enables the calculation of a three-dimensional image of a transirradiated volume situated around the isocenter.

In C-arm x-ray devices, the x-ray source and the image sensor are arranged opposite each other on a semicircular (thus C-shaped) carrier. This carrier, the C-arm, can be rotated in the direction of the C-arm circumference in an "orbital direction", and in a direction perpendicular to this. The patient or subject to be examined is situated substantially in the center of the C-arm, and various orientations of the x-ray beam, and therewith different two-dimensional projections of the transirradiated volume, can be generated via orbital and angular movement.

Two variants differ in C-arm x-ray devices. The first variant comprises an "isocentric C-arm" in which the rotation axis for the orbital motion that runs perpendicular to the plane of the C-arm runs through a point in common with the x-ray beam, namely the isocenter. This ensures that the x-ray beam always runs through the isocenter for each arbitrary orbital orientation, which (as stated above) enables the acquisition of two-dimensional image data that are immediately used to generate three-dimensional images.

The second variant comprises a non-isocentric C-arm in which the central x-ray beam runs through different volumes to be transirradiated for different orbital orientations. The use of the thusly acquired two-dimensional projections for generation of three-dimensional images is at most possible for a limited volume to be reconstructed. For this reason, non-isocentric C-arms exhibit the advantage that they are less expensive to construct and thus are easier and most cost-effective.

U.S. Pat. No. 6,382,835 by the applicant, herein incorporated by reference, discloses a C-arm x-ray device with a non-isocentric C-arm that can generate different orientations of the x-ray beam via angular rotation of the C-arm, and therewith can generate different two-dimensional projections from which a three-dimensional image can be generated. However, the angular motion also allows no large movement range like the orbital motion of the C-arm, which limits the possibilities to generate three-dimensional images.

SUMMARY OF THE INVENTION

The object of the invention is to fashion an x-ray device with a non-isocentric C-arm, such that the generation of two-dimensional projections of a transirradiated volume around an isocenter is enabled via movement of the C-arm in the orbital direction, and thus, in the circumferential direction.

The invention achieves this object via a C-arm x-ray device with non-isocentric C-arm that comprises a device for vertical adjustment of the C-arm and a device for horizontal adjustment of the C-arm, whereby the device for horizontal adjustment of the C-arm enables its adjustment in the horizontal direction within the plane in which the C-arm is located, and whereby both adjustment devices are fashioned such that, via the horizontal and vertical adjustment device, the central x-ray beam can be moved back into the isocenter after each orbital motion of the C-arm.

The invention also achieves this object by a method for operating a 3-D C-arm x-ray device, comprising: providing a non-isocentric C-arm on the x-ray device; positioning an x-ray source for producing an x-ray beam at an isocenter within the C-arm; and orbitally rotating the C-arm during an examination of the x-ray source and simultaneously adjusting at least one of a horizontal adjustment device and a vertical adjustment device of the C-arm so that the x-ray beam is moved to or stays at the isocenter.

A fundamentally easy and cost-effective C-arm x-ray detector with non-isocentric C-arm can thereby be used to generate two-dimensional projections of the always-identical x-ray volume, in order to generate a three-dimensional image of the transirradiation volume from the two-dimensional projections. The adjustment devices in the horizontal and vertical direction need only offer the possibility of a linear adjustment, and are correspondingly uncomplicated to realize.

In an advantageous embodiment of the invention, the movement of the central x-ray beam in the isocenter to be transirradiated is effected by an automatic control of the vertical and horizontal adjustment device. The generation of two-dimensional projections that are necessary to generate a three-dimensional image can thereby run fully automatically. Moreover, the automatic control of the adjustment devices enables an operator to set different orientations of the x-ray beam, for example, by hand, without thereby abandoning the transirradiated isocenter of the subject or patient to be examined.

DESCRIPTION OF THE DRAWINGS

Further advantages of embodiments of the invention illustrated in the picures.

DETAILED DESCRIPTION OF THE PREFERRED EMBODIMENTS

Figure 1:
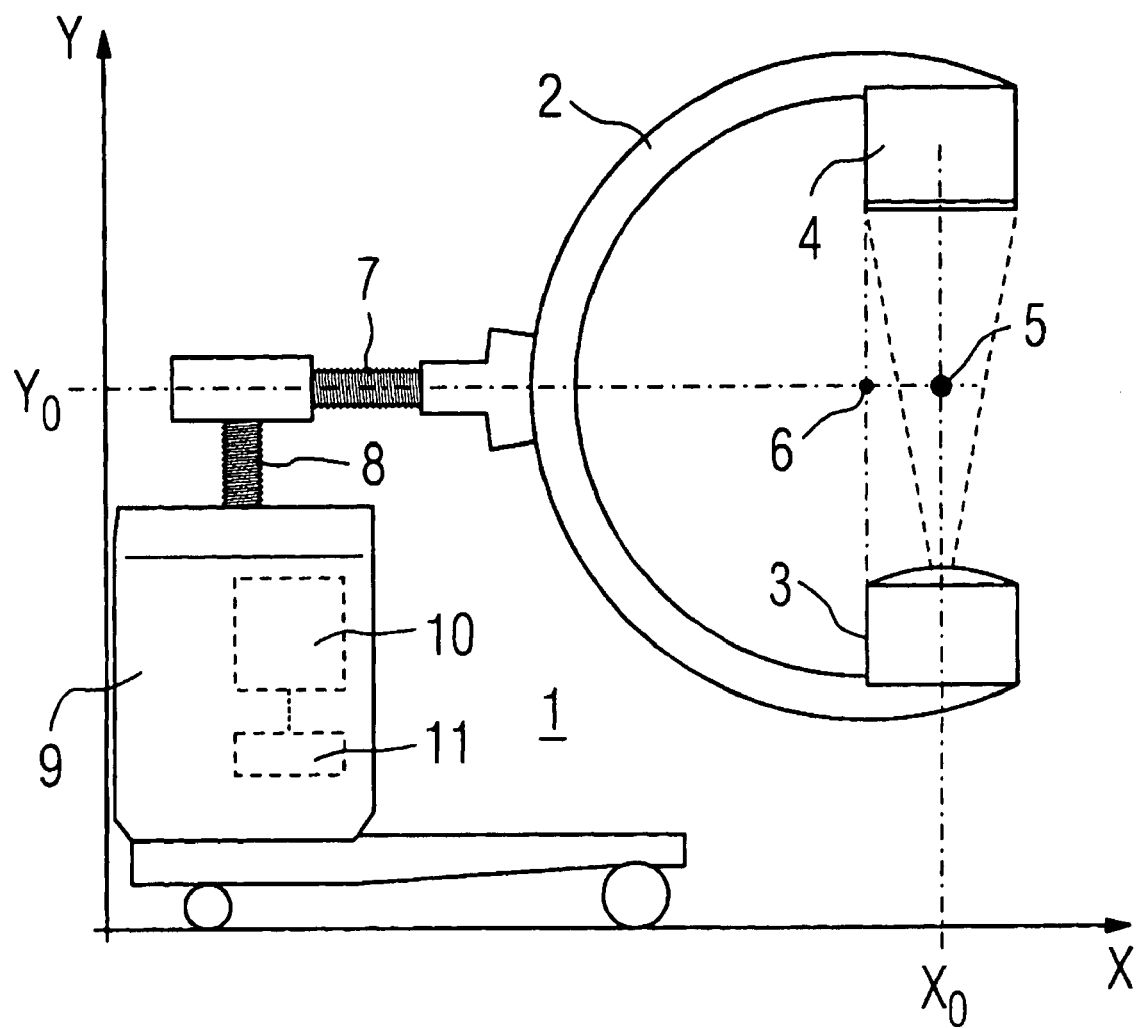
FIG. 1 is a schematic side view of a C-arm x-ray device with a vertically oriented x-ray beam.

A C-arm x-ray device 1 with a vertically oriented x-ray beam is shown in FIG. 1. The x-ray beam is indicated as a radiation beam via dashed lines between the x-ray source 3 and the image sensor 4. It runs through the "isocentric point" 5 that is likewise indicated in FIG. 1.

The C-arm x-ray device comprises a C-arm 2 that is fashioned non-isocentrically. Non-isocentric means that the rotation center 6 for rotation movements of the C-arm 2 is not identical with the isocenter 5. Rather, the rotation center 6 is situated horizontally near the isocenter 5, such that a rotation of the C-arm 2 in the orbital direction would also lead to a rotation of the isocenter 5 around the rotation center 6. This displacement of the isocenter 5 would make impossible the generation of three-dimensional images from various two-dimensional projections that are acquired via different orientations of the x-ray beam.

In order to overcome this problem, the C-arm x-ray detector 1 comprises a horizontal adjustment device 7 as well as a vertical adjustment device 8. The adjustment devices are motor-driven in an advantageous embodiment. The C-arm 2 can be adjusted in a horizontal direction via the horizontal adjustment device 7 and in the vertical direction via the vertical adjustment device 8. The isocenter 5 of the x-ray beam can thereby also be moved in the horizontal or vertical direction. In the indicated spatial coordinate system with the horizontal axis X and the vertical axis Y, the isocenter 5 can be moved in all spatial directions, and therefore unintended movements of the isocenter 5 around the rotation center 6 can be compensated given orbital motions of the C-arm 2.

The C-arm x-ray device 1 comprises a mobile carrier 9 that comprises the control and feed of all devices to move the C-arm 2, as well as some way to evaluation and display image data acquired by the image sensor 4. In a preferred embodiment, the mobile carrier 9 comprises a computer that can generate a three-dimensional image of the transirradiated volume around the isocenter 5 from various two-dimensional image projections of the isocenter 5 that have been acquired with different orientation of the x-ray beam.

In a further preferred embodiment, the mobile carrier 9 comprises an electronic control 10 that automatically controls the orientations of the x-ray beam necessary for generation of two-dimensional image projections or the adjustment of the C-arm in the horizontal and vertical direction to maintain the position of the isocenter 5. In a particularly advantageous embodiment, the electronic control 10 is fashioned as a computer; it can, moreover, be identical to the computer for generating image data. It automatically controls the vertical adjustment device 8, the horizontal adjustment device 7, and the adjustment device (not shown in the image) for orbital motions of the C-arm. The horizontal and vertical adjustment can thereby ensue synchronously.

The electronic control controls the adjustment devices 7 and 8 dependent on a signal (that depends on the orbital angle of the C-arm 2) of an angle transmitter on the C-arm 2. The adjustment of the C-arm 2 in the horizontal and vertical direction depends, in a predetermined interrelationship fixed by the mechanical relationships, on its orbital position. This fixed, predetermined interrelationship is reproduced in the electronic control 10 and serves for the corresponding fixed, predetermined control of the horizontal and vertical adjustment device 7 and 8. Stated more precisely, the necessary compensation movement to compensate an undesired displacement of the rotation center 6 depends on the orbital rotation angle, and thus on the change of the orbital position. The electronic control 10 can control the automatic execution of a horizontal and vertical compensation movement dependent on the change of the rotation angle.

In a further preferred embodiment, the electronic control 10 is fashioned such that it automatically compensates movements of the isocenter 5 from its current position, for example due to a manual orbital rotation of the C-arm 2, via a horizontal and vertical adjustment. For example, an operating personnel can manually provide a desire orientation of the x-ray beam without having to worry about maintaining the isocenter 5. The stationary maintenance of the isocenter 5 is automatically ensured by the electronic control 10 in the mobile carrier 9.

In order to be able to compensate undesired motion of the isocenter 5 via the horizontal and vertical adjustment, the electronic control 10 in the mobile carrier 9 has access to a characteristics storage 11 in which characteristics are stored from which, starting from any orbital position, the necessary horizontal and vertical compensation motions can be extracted. Using these characteristics, the electronic control 10 can automatically determine the necessary control commands for the vertical adjustment device 8 and the horizontal adjustment device 7 and transmit these to them.

In a particular case, it is possible that specific orbital positions of the C-arm 2 can no longer be compensated by orbital motions of any kind in the event that the adjustment devices 7 and 8 have encountered a limit to their adjustment range. In an advantageous embodiment, the electronic control 10 can therefore have additional access to characteristics to determine the limits of the adjustment range. Moreover, it can have access to characteristics for an initial state of the adjustment devices 7 and 8; the displacement of the isocenter 5 for orbital motions of any kind can be compensated from the initial state. The electronic control 10 can decide that this initial state is automatically taken up when needed or at the beginning of each use of the C-arm device 1.

In the indicated spatial coordinate system with the horizontal axis X and the vertical axis Y, the stationary isocenter 5 exhibits the position $(X_0/Y_0)$.

Figure 2:
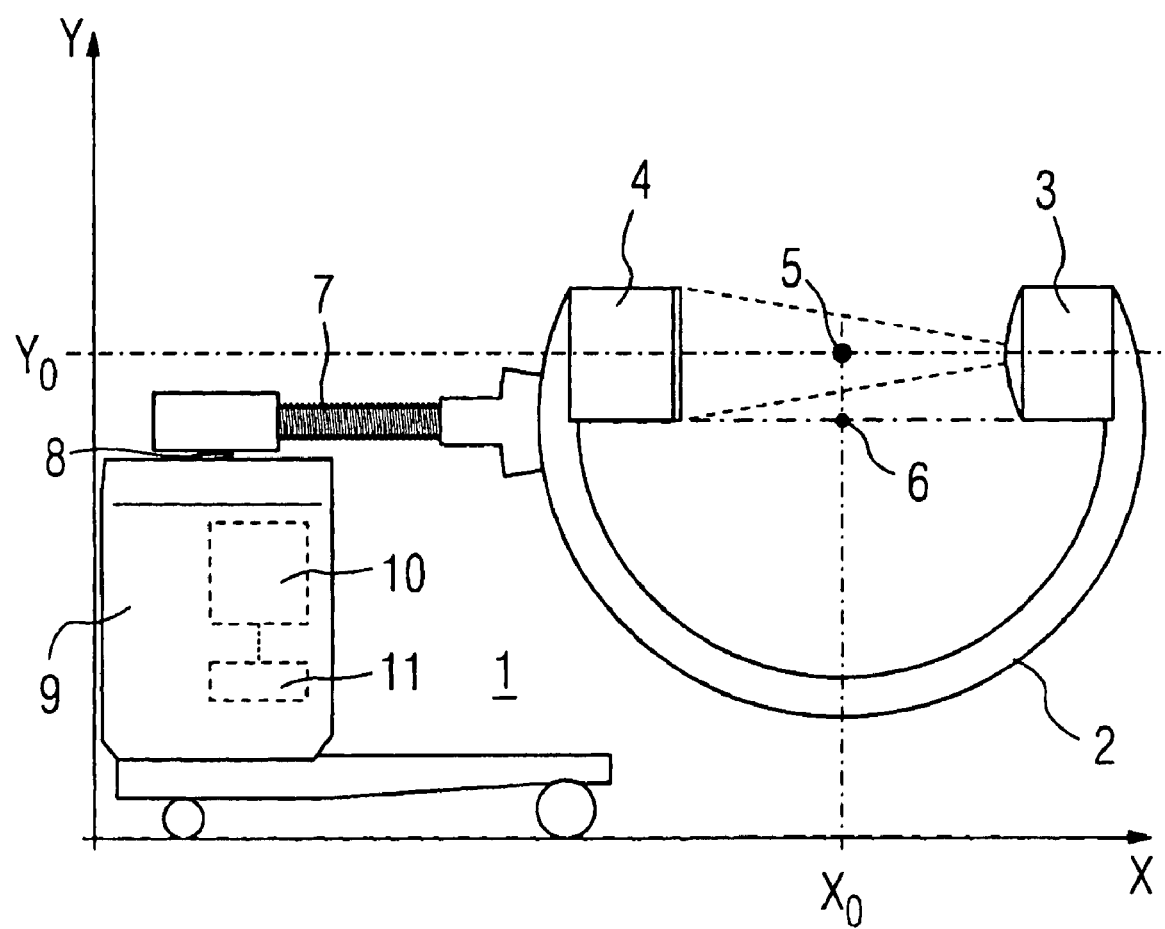
FIG. 2 is a schematic side view of a C-arm x-ray device with a horizontally oriented x-ray beam.

The C-arm x-ray device 1 with a horizontally oriented x-ray beam is shown in FIG. 2. For the rest, the C-arm x-ray device 1 is identical to the device shown in the preceding illustration, and as such, the same reference characters are used.

The horizontal orientation of the x-ray beam has been effected via a counterclockwise orbital motion of the C-arm 2. In addition to the orientation of the x-ray beam due to the non-isocentric design of the C-arm 2, the spatial association of the isocenter 5 with the rotation center 6 also changes via the orbital motion of the C-arm 2. In the shown embodiment, the isocenter 5 migrates around the rotation center 6 in the direction of the orbital motion. In comparison to the preceding specified image, the isocenter would therefore have been displaced up and to the left in the spatial coordinate system. This undesired displacement of the isocenter 5 is, however, compensated via horizontal and vertical adjustment of the C-arm 2.

The isocenter 5 is situated as before at the spatial coordinate point $(X_0/Y_0)$, while a motion of the rotation center 6 ensues instead of a motion of the isocenter 5 via the compensation movement in the horizontal and vertical direction. The rotation center 6 is now arranged displaced down and to the right from its position shown in FIG. 1. In comparison to FIG. 1, the adjustment of the C-arm 2 is also visible on the length of the horizontal adjustment device 7 and of the vertical adjustment device 8. Since, due to the orbital motion to the left, the isocenter 5 would have thus been moved on the mobile carrier 9, the horizontal adjustment device 7 has deployed to compensate this motion, and is now extended with regard to the preceding image. The vertical adjustment device 8 is correspondingly shortened.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A C-arm x-ray device, comprising:
    an x-ray source producing a central x-ray beam;
    a non-isocentric C-arm on which the x-ray source is positioned and that can be orbitally rotated, wherein, for an orbital rotation alone, there is no common isocenter point through which the central x-ray beam passes while rotating;
    the C-arm x-ray device comprising:
    a horizontal adjustment device that horizontally adjusts the C-arm which enables an adjustment of the C-arm within a plane of the C-arm; and
    a vertical adjustment device that vertically adjusts the C-arm;
    the horizontal adjustment device and the vertical adjustment device being configured such that they can automatically move the central x-ray beam of the x-ray source back into a common isocenter, given an orbital rotation of the C-arm.

2. The C-arm x-ray device according to claim 1, further comprising:
    an electronic control that controls the horizontal and vertical adjustment devices.

3. The C-arm x-ray device according to claim 2, wherein the electronic control is fashioned as a computer.

4. The C-arm x-ray device according to claim 2, further comprising:
    a characteristic storage that is connected with the electronic control.

5. The C-arm x-ray device according to claim 4, further comprising:
    characteristics stored within the characteristic storage comprising values related to a horizontal and a vertical compensation movement, compensation being made dependent on a change of a rotation angle of the C-arm.

6. The C-arm x-ray device according to claim 5, further comprising:
    a mechanism that determines, before an automatic execution of a compensation movement, a limit of an adjustment range of the C-arm, dependent on a change of a rotation angle, a vertical position and a horizontal position of the C-arm.

7. A method for operating a 3-D C-arm x-ray device, comprising:
    providing a non-isocentric C-arm on the x-ray device wherein, for an orbital rotation alone, there is no common isocenter point through which a central x-ray beam of an x-ray source passes while rotating;
    positioning the x-ray source for producing the x-ray beam at an isocenter within the C-arm; and
    orbitally rotating the C-arm during an examination of the x-ray source and simultaneously adjusting at least one of a horizontal adjustment device and a vertical adjustment device of the C-arm so that the x-ray beam is moved to or stays at the isocenter.

8. The method according to claim 7, further comprising:
    storing characteristics in a characteristic storage comprising values related to a horizontal and a vertical compensation movement.

9. The method according to claim 8, further comprising:
    accessing the values related to the horizontal and vertical compensation movement with an electronic control; and
    automatically making the adjustments with the electronic control dependent on a change of a rotation angle.

* * * * *